US006258796B1

(12) United States Patent
Richards

(10) Patent No.: US 6,258,796 B1
(45) Date of Patent: Jul. 10, 2001

(54) WATER SOLUBLE LIPIDATED ARABINOGALACTAN

(75) Inventor: Geoffrey N. Richards, Missoula, MT (US)

(73) Assignee: The University of Montana, Missoula, MT (US)

(*) Notice: Subject to any disclaimer, the term of this patent is extended or adjusted under 35 U.S.C. 154(b) by 0 days.

(21) Appl. No.: 09/174,232

(22) Filed: Oct. 16, 1998

Related U.S. Application Data

(62) Division of application No. 08/754,225, filed on Nov. 20, 1996.

(51) Int. Cl.⁷ .............................. A61K 31/715; C07H 1/00
(52) U.S. Cl. ......................... 514/53; 514/54; 536/123.1; 536/123.13
(58) Field of Search .................... 536/123.1, 123.3; 514/53, 54

(56) References Cited

U.S. PATENT DOCUMENTS

| | | | |
|---|---|---|---|
| 4,707,471 | 11/1987 | Larm et al. | 514/54 |
| 4,735,935 | 4/1988 | McAnalley | 514/53 |
| 4,851,224 | 7/1989 | McAnalley | 424/195.1 |
| 4,877,611 * | 10/1989 | Cantrell | 514/885 |
| 4,917,890 | 4/1990 | McAnalley | 424/195.1 |
| 4,957,907 | 9/1990 | McAnalley | 536/123 |
| 4,959,214 | 9/1990 | McAnalley | 424/195.1 |
| 4,966,892 | 10/1990 | McAnalley | 514/54 |
| 5,106,616 | 4/1992 | McAnalley et al. | 424/85.2 |
| 5,116,969 | 5/1992 | Adams et al. | 536/128 |
| 5,118,673 | 6/1992 | Carpenter et al. | 514/54 |
| 5,284,833 | 2/1994 | McAnalley et al. | 514/23 |
| 5,308,838 | 5/1994 | McAnalley et al. | 514/54 |
| 5,409,703 | 4/1995 | McAnalley et al. | 424/435 |
| 5,441,943 | 8/1995 | McAnalley et al. | 514/54 |
| 5,443,830 | 8/1995 | Moore et al. | 424/195.1 |
| 5,554,386 * | 9/1996 | Groman et al. | 514/54 |
| 5,756,098 | 5/1998 | Price et al. | 210/632 |
| 5,882,520 | 3/1999 | Richards et al. | 424/195.1 |

FOREIGN PATENT DOCUMENTS

| | | |
|---|---|---|
| 4136325 A1 | 5/1993 | (DE) . |
| 2260333 * | 4/1993 | (GB) . |
| 58-190365 | 11/1983 | (JP) . |
| 60-233560 | 11/1985 | (JP) . |
| 01054001 | 3/1989 | (JP) . |
| WO 93/08810 | 5/1993 | (WO) . |
| WO 93/25239 | 12/1993 | (WO) . |
| WO 95/12620 | 5/1995 | (WO) . |
| WO 96/09309 | 3/1996 | (WO) . |

OTHER PUBLICATIONS

K. Bienvenu et al., "Leukotriene B₄ Mediates Shear Rate–Dependent Leukocyte Adhesion in Mesenteric Venules," *Cir. Res.*, 71:906–911 (1993).

S. Borman et al.,"Glycotechnology Drugs Begin to Emerge from the Lab," *C & EN*, pp. 27–34 (Jun. 28, 1993).

S. E. Bucklin et al., "Therapeutic Efficacy of a Polymyxin B–Dextran 70 Conjugate in Experimental Model of Endotoxemia," *Antimicrobial Agents & Chemotherapy*, 39:1462–1466 (1995).

S. M. Buttrum et al., "Selectin–Mediated Rolling of Neutrophils on Immobilized Platelets," *Blood*, 82: 1165–1174 (1993).

Carter et al., "Drugs Available to Treat Cancer," *Principles of Cancer Treatment*, Ed. Carter et al., Chapter 10, pp. 111–145 (1982).

M. Dore et al., "P–Selectin Mediates Spontaneous Leukocyte Rolling in Vivo," *Blood*, 82: 1308–1316 (1993).

D. E. Hahn et al., "Development of an Equilibrium Dialysis Technique for Quantifying Start–Lipid Complexes," *Cereal Chemistry*, 64: 77–80 (1987).

V. Glaser, "Work on Cell–Adhesion–Based Interactions Beginning to Bear Fruit," *Genetic Engineering News*, pp. 6–8 (1995).

A. Gunnarsson, "N–and O–Alkylation of Glycoconjugates and Polysaccharides by Solid Base in Dimethyl Sulphoxide/Alkyl Iodide," *Glycoconjugate J.*, 4: 239–245 (1987).

B. Hagmar et al., "Effect of Arabinogalactan and Other Glycoconjugates on Experimental Metastases," *Cellular Pharmacology*, 1:87–90 (1984).

S. A. Hamburger et al., "GMP–140 Mediates Adhesion of Stimulated Platelets to Neutrophils," *Blood*, 75:550–554 (1990).

C. Harris et al., "Efficacy of Acemannan in Treatment of Canine and Feline Spontaneous Neoplasms," *Mol. Biother.*, 3: 207–213 (1991).

J. E. Hodge, "Improving Reactivity with Pyridine," *Methods in Carbohy. Chem.*, vol. 4, Ed. R. L. Whistler, A.P. pp. 281–282 (1964).

(List continued on next page.)

*Primary Examiner*—Howard C. Lee
*Assistant Examiner*—Everett White
(74) *Attorney, Agent, or Firm*—Mueting, Raasch & Gebhardt, P.A.

(57) ABSTRACT

Arabinogalactan compositions are provided which are useful in a wide variety of different biomedical applications. In one embodiment, water soluble lipidated arabinogalactans are provided which include arabinogalactan with a limited proportion of lipophilic groups, such as long-chain hydrocarbon groups, covalently attached to free hydroxyl groups on the arabinogalactan. The lipidated arabinogalactans are water soluble and biocompatible and are useful for a wide variety of different biomedical applications. The lipidated arabinogalactans can be used, for example, to inhibit cell adhesion, and to inhibit infection or inflammation. The lipidated arabinogalactans further may be used as adjuvants, to inhibit metastasis, and in other therapeutic applications.

18 Claims, No Drawings

OTHER PUBLICATIONS

K. Ley et al., "Lectin–Like Cell Adhesion Molecule 1 Mediates Leukocyte Rolling in Mesenteric Venules in Vivo" *Blood*, 77:2553–2555 (1991).

Y. Manabe et al., "Production of a Monoclonal Antibody–Mitomycin C Conjugate, Utilizing Deztran T–40, and its Biological Activity," *Biochemical Pharmacology*, 34: 289–291 (1985).

T. N. Mayadas et al., "Leukocyte Rolling and Extravasation are Severely Compromised in P Selectin–Deficient Mice," *Cell*, 74: 541–554 (1993).

R. P. McEver, "Leukocyte–Endothelial Cell Interactions," *Current Opinion in Cell Biology*, 4: 840–849 (1992).

R. P. McEver, "Misguided Leukocyte Adhesion," *J. Clin. Invest.*, 91:2340–2341 (1993).

G. Mocanu et al., "Macromolecular Drug Conjugates II. Metronidazole–Dextran Prodrugs," *Journal of Bioactive and Compatible Polymers*, 8: 383–392 (1993).

S. D. Rosen, "The LEC–CAMS: An Emerging Family of Cell–Cell Adhesion Receptors Based Upon Carbohydrate Recognition," *Am. J. Respir. Cell. Mol. Biol.*, 3: 397–402 (1990).

A. W. Stout, "Larch Arabogalactan, " Chapter XII, *Industrial Gums*, Ed. R. L. Whistler, pp. 307–310 (1959).

L. J. Tanghe et al., "Cellulose Acetate: Acetylation of Cellulose," *Methods in Carbohy. Chem.*, vol. 3, Ed. R. L. Whistler, A. P. pp. 193–198 (1963).

R. N. Tharanatha et al., "Physico–Chemical Characteristics of Starches from Sal (*Shorea Robusta*) and Dhupa (*Vateria Indica*) Seeds," *Starch/Stärke*, 42: 247–251 (1990).

Cera et al., "Anthracycline Antibiotics Supported on Water–Soluble Polysaccharides: Synthesis and Physiochemical Characterization," *Int. J. Biol. Macromol.*, 10:66–74 (1988).

Title page, copyright page and p. 306 of Cotran et al., *Robbins Pathological Basis of Disease, 5th Edition*, W. D. Saunders Company, Philadelphia, PA (1994).

Title page,copyright page and p. 1225 of *Hawley's Condensed Chemical Dictionary, Twelfth Edition*, Van Nostrand Reinhold Company, New York, NY (1993).

Marshall et al., "Human Cytokines Induced by Acemannan," Presented at American Academy of Allergy and Immunology, Chicago, IL (1993).

\* cited by examiner

WATER SOLUBLE LIPIDATED ARABINOGALACTAN

This appln is a Divisional of Ser. No. 08/754,225 filed Nov. 20, 1996.

BACKGROUND OF THE INVENTION

The present invention is generally in the area of methods for making polysaccharides which include attached lipophilic groups, but which remain water-soluble.

Modified polysaccharides have been isolated from natural sources or synthesized chemically and their biological activities studied. Starches containing bound protein and lipid groups have been isolated from plant components such as seeds. See, e.g., Tharanathan et al., Starch, 42:247–251 (1990).

Fatty acid esters of polysaccharides have been produced by treatment of the polysaccharides with fatty acid chlorides or anhydrides or by ester exchange, and the alkyl ethers of polysaccharides have been produced by several methods (Methods in Carbohydrate Chemistry, vol. II (1963) Ed., R. L. Whistler and M. L. Wolfrom, Academic Press, New York; Section VI and V). However, most previous studies of this type have involved high degrees of derivatization with relatively short hydrocarbon chains, such as acetate esters or methyl ethers. Highly derivatized products of this type are generally water-insoluble. JP 60233560 to Fujirebio K. K. discloses a method of measuring lipase activity using as the enzyme substrate a water soluble fatty acid ester of a low molecular weight oligosaccharide such as dextran. JP 87209721 to Sugiyama Industrial Chemical Institute discloses the preparation of water soluble fatty acid esters of hydrolyzed starch for use as emulsifiers and detergents.

The synthesis of cyclodextrin derivatives, modified by the attachment of fatty acids or alcohols, which may be used as bile acid absorption agents, is described in DE 4 136 325 to Ahlers et al. PCT WO 95/12620 to Alpha-Beta Technology, Inc. discloses derivatized polysaccharide bile acid sequestrants for reducing cholesterol which include a hydrophobic, cationic ligand coupled to a polysaccharide substrate.

Acetylated mannans "acemannans" are long-chain polydispersed beta-1,4-linked mannan polymers interspersed with O-acetyl groups which are isolated from the Aloe vera leaf. Acemannans have been reported to have antitumor activity and to be useful as adjuvants. Harris et al., Mol. Biother. 3:207–213 (1991). Acetylated mannans also have been reported to be useful for regulating blood cholesterol levels; for reducing inflammation and infection; as an immunostimulant; and as an antiviral. U.S. Pat. Nos. 5,441,943 and 5,308,838 to Carpenter et al.; PCT WO 93/08810 to Carrington Lab, Inc.; and U.S. Pat. Nos. 5,118,673 and 5,106,616 to Carpenter et al. Acemannans also have been shown to induce human cytokines. Marshall et al., Abstract presented at the American Academy of Allergy and Immunology, Chicago, Ill., March, 1993.

It is an object of the invention to provide lipid-modified polysaccharides which are water-soluble, biocompatible and can be used in a variety of different biomedical applications. It is a further object of the invention to provide water soluble, lipid-modified forms of arabinogalactan which can be used in different applications, for example, to promote the formation of stable emulsions, to increase drug solubility, and to serve as adjuvants. It is another object of the invention to provide methods for making and using a range of such modified forms of arabinogalactan in different biomedical applications.

SUMMARY OF THE INVENTION

Arabinogalactan compositions are provided which are useful in a wide variety of different biomedical applications. In one embodiment, water soluble lipidated arabinogalactans are provided which include arabinogalactan with a limited proportion of hydrophobic groups, such as long-chain hydrocarbon groups, covalently attached to free hydroxyl groups on the arabinogalactan. The lipidated arabinogalactans are water soluble and biocompatible and are useful in a wide variety of different biomedical applications. The lipidated arabinogalactans can be used, for example, to inhibit cell adhesion, and to inhibit infection or inflammation. The lipidated arabinogalactans further may be used as adjuvants, to inhibit metastasis, and in other therapeutic applications.

DETAILED DESCRIPTION OF THE INVENTION

Water soluble lipidated forms of arabinogalactan are provided which are useful in a wide variety of different applications, particularly biomedical applications. Water soluble lipidated arabinogalactan may be used for example, to form stable emulsions, to increase the solubility of sparingly water soluble drugs, to inhibit cell adhesion, for metastasis control, as a bile acid sequestrant, or as an adjuvant. The lipidated arabinogalactan includes a limited proportion of lipophilic groups, such as long chain hydrocarbons bonded to the polysaccharide, e.g., by ether or by ester linkages, to modify its biological activity, while advantageously retaining water solubility properties. Due to the water solubility and low toxicity, the lipidated arabinogalactans are useful in a wide range of therapeutic applications.

Arabinogalactan

Arabinogalactan ("AG") is a water-soluble polysaccharide which can be isolated from trees of the genus Larix, particularly Larix occidentalis (western larch). Arabinogalactan may constitute up to 35% of the total heartwood of some species. Stout, "Larch Arabinogalactan" in Industrial Gums, R. L. Whistler Ed., Academic Press, New York, pp. 307–310, 1959. It is highly water soluble and can be purified from larch chips.

As used herein, the term "arabinogalactan," unless otherwise specified, includes naturally occurring or synthetic arabinogalactan, portions of arabinogalactan, such as degradation products, and chemically or biochemically modified arabinogalactan or portions thereof which have been modified using methods available in the art.

In one preferred embodiment, ultrarefined arabinogalactan is used to form the lipidated water soluble arabinogalactan compositions. Methods for the preparation of ultrarefined arabinogalactan are disclosed in U.S. Pat. No. 5,116,969, the disclosure of which is incorporated herein by reference. Ultrarefined arabinogalactan of greater than 95%, or optionally, greater than 99.9% purity (Larex UF™) is available from Larex, International, St. Paul, Minn. As defined herein "ultrarefined arabinogalactan" refers to arabinogalactan, isolated from a plant source such as trees of the genus Larix, with a purity greater than 95%. In a preferred embodiment, the molecular weight of the ultrarefined arabinogalactan is between about 10,000 and 30,000 daltons (by size exclusion chromatography with pullulan reference).

Arabinogalactan from Larix trees is useful since it is extremely water-soluble, occurs naturally with a very narrow molecular weight distribution, and is highly branched and thus not subject to viscosity problems. Arabinogalactan also is highly biocompatible and is non-toxic.

Water Soluble Lipidated Arabinogalactan

Structure

Lipidated arabinogalactan molecules which include attached lipophilic groups but which are water soluble are provided. Preferably the solubility of the lipidated arabinogalactan compound is at least about 0.1%. As used herein, the phrase "lipidated arabinogalactan" refers to arabinogalactan covalently attached to a lipophilic group. Preferred lipophilic groups include long chain hydrocarbon groups. Other lipophilic groups include steroids, terpenes, fat soluble vitamins, phytosterols, terpenoids, phospholipids, glycerols, and natural or synthetic fats. The lipophilic group may be attached to the arabinogalactan either directly or via a linking group. For example, the free hydroxy groups on the arabinogalactan may be linked to hydrocarbon chains via an ether or ester linkage.

The water soluble lipidated arabinogalactan is defined in one embodiment by the formula:

AG-R-L where:

AG is arabinogalactan;

L is a lipophilic group, preferably a branched or straight chain saturated or unsaturated hydrocarbon including between about one to 90 carbons, for example between about 4 and 30 carbons, or alternatively between about 10 and 20 carbons, and is most preferably a $C_4$–$C_{30}$ straight chain saturated hydrocarbon, for example $C_{10}$–$C_{18}$ straight chain hydrocarbon; and R is a group linking the AG to the lipophilic group, preferably an ester or ether bond between a hydroxyl on the AG and a carboxyl or hydroxyl on the lipophilic group. The R group linking AG and L also may be or contain functional groups such as esters, thioesters, ethers, sulfonic acid esters, carbonates, thiocarbomates, carbamates and thiocarbamates.

The water soluble lipidated arabinogalactan is formed by attaching lipophilic groups to a portion of the free hydroxyl groups on the arabinogalactan. For example, long chain hydrocarbon carboxylic acid molecules, having the formula $HOOC[CH_2]_nCH_3$ where n is between 4 and 30, may be attached to the free hydroxyl groups on the arabinogalactan. Alternatively, n may be less than 4, for example, between 1 and 3, or greater than 30, for example between 30 and 90. Additionally, the arabinogalactan sample may include different attached lipophilic groups.

The degree of substitution of arabinogalactan preferably is between about 0.01% to 15%, for example, 0.1% to 5%, or optionally between about 1–3%. As used herein, the phrase "degree of substitution" or "DS" refers to the percentage of glycose units in an arabinogalactan sample which carry a lipophilic group, assuming that all of the glycose units which are substituted are monosubstituted. In a preferred embodiment, the esterification is carried out in solution which promotes uniform distribution of ester groups.

The degree of substitution of lipophilic hydrocarbon molecules on the arabinogalactan can be designed and modified for different applications. It is preferred that the degree of substitution of hydrocarbon groups on the lipidated arabinogalactan not be so great as to render the arabinogalactan non-water soluble. In one preferred embodiment, the degree of substitution is as great as possible without resulting in making the complex of the arabinogalactan non-water soluble or poorly soluble in water. The use of arabinogalactan is advantageous, because a relatively large degree of substitution with lipophilic hydrocarbons is possible, e.g., 0.1 to 5%, without loss of water solubility properties. The water solubility is an important property of the lipidated arabinogalactan. It is preferred that the water solubility of the lipidated arabinogalactan be at least about 0.1%, for example, in one preferred embodiment, between 2 and 40 g/mL. Long-chain esters of polysaccharides previously prepared have been primarily water-insoluble. More heavily lipidated AG palmitate is water insoluble and inactive in certain applications for example as an adjuvant.

Synthesis

The lipidated arabinogalactan may be formed using organic chemistry reactions available in the art, such as esterification reactions or etherification reactions, to couple lipophilic groups such as hydrocarbons to the polysaccharide.

Esterification

The water-soluble lipidated arabinogalactan is formed in one embodiment by the covalent attachment of long-chain hydrocarbons to the arabinogalactan via an ester linkage. In the esterification reaction, the arabinogalactan or derivative thereof is reacted with an anhydride or acid chloride of a long chain carboxylic acid. In the reaction, partial esterification of the free hydroxy groups in the arabinogalactan with the long chain carboxylic acid occurs.

Fatty acids which can be reacted, for example, in anhydride or acid chloride form, with arabinogalactan ("AG"), in the esterification reaction include palmitate, stearate, and decanoate. Exemplary compounds which can be formed include AG palmitate, AG stearate and AG decanoate. The preferred degree of substitution for the AG with the hydrocarbon fatty acids is between about 0.01 and 15%, and in one preferred embodiment is between 0.1 and 5%.

Etherification

The water soluble lipidated arabinogalactan also may be formed in an etherification reaction. Partial ethers may be formed by the reaction of a arabinogalactan, or a derivative thereof, with long chain alkyl halides or epoxides under alkaline catalysis. For example, the water-soluble dodecyl ether of arabinogalactan, with a degree of substitution ("DS") of 2.6% may be formed by reaction with dodecyl iodide.

Adjuvants

In one embodiment, the lipidated arabinogalactan may be used as an adjuvant to enhance the immunogenicity of an antigen, such as a virus. The immunogenic composition including the antigen and lipidated arabinogalactan can be administered by any method known to those skilled in the art, that does not denature or inactivate the antigen contained in the composition including oral, transmembrane and transmucosal administration. Preferably, the composition is administered parenterally (such as intravenously, intramuscularly, intraperitoneally), most preferably subcutaneously. The composition including a mixture of the antigen and the lipidated arabinogalactan may be administered in combination with suitable physiologically acceptable carriers known to those skilled in the art, such as water or saline. The antigen and lipidated arabinogalactan also may be administered separately, or, in another embodiment may be covalently conjugated prior to administration.

The antigen can be a cell, bacteria, or virus particle, or portion thereof, a hormone, a growth factor or an immunogenic synthetic, recombinant or naturally occurring protein or peptide. Other examples include an influenza protein, tetanus toxoid, an HIV protein, a hepatitis B protein and a neisseria gonorrhea protein.

Lipidated arabinogalactan is useful as an adjuvant due to its low toxicity, in comparison to many other available immunoadjuvants. Many adjuvants, such as Freund's Complete Adjuvant, are toxic. Freund's adjuvant for example, causes granulomatous lesions in animals at the site of immunization and may also cause the recipient of a vaccine to test positive for tuberculosis, and therefore is only useful for animal research purposes, not human vaccinations.

A preferred form of a water soluble lipidated arabinogalactan for use as an adjuvant is arabinogalactan substituted with a hydrocarbon group including between about 10 to 18 carbons, wherein the degree of substitution is about 2%. For example, AG palmitate, with a degree of substitution of about 2%, may be used as an adjuvant.

Increasing the Water Solubility of Drugs

The water soluble lipidated arabinogalactan may be used to increase the water solubility of drugs which have low solubility in water, by providing the drug in an aqueous solution of lipidated arabinogalactan. For example, the concentration of the lipidated arabinogalactan in the aqueous solution of the drug may be about 0.1 to 20%. The enhancement of the solubility of a sparingly water soluble drug is described in Example 8.

The water solubility of any of a wide range of therapeutic agents can be increased including small organic molecules proteins, peptides, and nucleic acids. Exemplary drugs include drugs effecting the nervous system, hormones, analgesics, antiinflammatory agents, diuretics, antidiuretics, antianginal agents, antihypertensive agents, antibiotics, antineoplastic agents, immunomodulators, hematopoietic agents, steroids including estrogens and progestins, and vitamins.

The water solubility of sparingly soluble antineoplastic agents including alkylating agents, steroids, antimetabolites, antimitotics, DNA intercalators, enzyme inhibitors, DNA synthesis inhibitors, and lytic agents can be improved. Illustrative agents include paclitaxel, mitomycin, cisplatin, flutamide, and other lipophilic agents, as described, for example in Carter and Livingston, Drugs Available to Treat Cancer, in Principles of Cancer Treatment, Carter et al., Eds., Chapter 10, pp 111–145, 1982, McGraw-Hill, N.Y.

Cell Adhesion

The water soluble lipidated arabinogalactan can be used in one embodiment to inhibit cell-adhesion, thereby to prevent or reduce inflammation or infection.

Inhibition of Infection

The arabinogalactan compounds may be used to inhibit infection of cells by invading microorganisms by interfering with the binding of the microorganism. Microorganism adherence to and subsequent invasion of cells during infection is mediated by the binding of proteins on the surface of the pathogen to animal cell surface oligosaccharides. Antiadhesive drugs operate to prevent cell infection by binding to the proteins on the pathogen and preventing the organism from binding to and infecting the cell, with the result that the pathogen, such as a bacteria, is washed away by natural processes which occur on mucosal surfaces for the clearing of bacteria. Borman, *Chemical and Engineering News*, Jun. 28, 1993, pp. 27–34, the disclosure of which is incorporated herein by reference.

Inhibition of Inflammation

In another embodiment, the arabinogalactan compounds may be used to inhibit abnormal inflammation underlying many pathological states such as rheumatoid arthritis, psoriasis, septic shock, atherosclerosis, thrombosis, ischemia and reperfusion injury.

Leukocyte-endothelial cell interactions in the anti-inflammatory response are mediated by complex signalling and adhesion molecules as described, for example, in McEver, *Current Opinion in Cell Biology*, 4:840–849 (1992), the disclosure of which is incorporated herein by reference. In the anti-inflammatory response, white blood cells are recruited to sites of inflammation on endothelial cells lining the blood vessel wall. The arabinogalactan compounds may operate by interfering with the binding of the white blood cells to the endothelial cell surface of the blood vessel wall. The water-soluble lipidated arabinogalactans are especially useful in inhibiting the adhesion of neutrophils to human endothelial cells. This can occur without interference with the binding of lymphocytes with beneficial effects in treatment of reperfusion injury for example in heart attacks, angioplasty or graft rejection. The suppression of inflammatory response may also be useful in treatment of back injuries.

Emulsifiers and Surfactants

The water soluble lipidated arabinogalactan may be used to form stable emulsions, or may be used as surfactants.

Bile Acid Sequestrants for Reducing Cholesterol

The water soluble lipidated arabinogalactan may be used as an agent for sequestering bile acids to reduce cholesterol. Bile acid sequestrants can be used to treat hypercholesterolemia by binding bile acids in the intestine after oral administration and then carrying them through the small intestine and causing them to be excreted. Water-soluble lipidated arabinogalactan may be designed and synthesized with attached lipophilic groups, such as hydrocarbon groups and then tested in vitro for bile acid binding ability using assays available in the art. Water-insoluble lipidated polysaccharides of high substitution (DS>20) have previously been used for this purpose, as described in PCT WO 95/12620 to Alpha-Beta Technology, the disclosure of which is incorporated herein by reference, however the use of water-soluble, lipidated polysaccharides of a low degree of substitution was not disclosed.

Metastasis Control

Arabinogalactan has been shown to reduce tumor metastases in mice, as described in Hagmar et al., *Cellular Pharmacology*, 1:87–90, 1994, the disclosure of which is incorporated herein by reference. Water-soluble lipidated arabinogalactan can be used to enhance the effect of arabinogalactan in this application. The lipidated arabinogalactan may be used to reduce metastasis of tumor cells from different malignancies, including carcinomas, lymphomas, and sarcomas, which can metastasize to distant sites through the vasculature.

Advantages of Arabinogalactan

Arabinogalactan has unique advantages over other polysaccharides for many applications including those mentioned above. It is extremely water-soluble and its concentrated solutions (e.g. 40%) have low viscosity. Thus when lipid groups are attached to the molecule it can carry a higher proportion of such groups, while maintaining water-solubility, compared, e.g., with starch or cellulose derivatives. Also, the aqueous solutions of the lipidated derivatives are not viscous and are therefore more biocompatible. The unusually highly branched structure of the arabinogalactan also offers exceptional steric accessibility for derivatization and favorable geometry for the lipid derivatives in solution.

The present invention will be further understood by reference to the following non-limiting examples.

Example 1: Assay of Adjuvant Activity of Lipidated Arabinogalactan

The adjuvant activities of the three arabinogalactan compounds, arabinogalactan ("AG"), low substitution (DS 1.7%) AG palmitate (water soluble), and high substitution (DS 7.3%) AG palmitate (water insoluble) were compared. In the experiment, 25 µg of ovalbumin ("O.A.") was injected into mice in a saline solution together with 50, 10, 2 or 0 µg (the control) of the arabinogalactan compounds. The animals were prebled prior to immunization; injected; bled on days 7 and 14; given a booster injection on day 21; and bled on days 28 and 35 for antibody determination. All three arabinogalactan compounds showed some adjuvant activity in antibody formation in comparison to the control. The low substitution AG palmitate had the highest adjuvant activity, however it was 10 to 100 fold weaker than that of comparable doses of a potent adjuvant, such as monophosphoryl lipid A. However, the latter is potentially toxic, extremely expensive, and being water-insoluble, requires complex formulation.

Example 2: Inhibition of Cell Adhesion by Arabinogalactans

The effect of Compounds A–F, listed below in Table 1, including arabinogalactan, and arabinogalactan with varying degrees of substitution (DS) of long hydrocarbon chain fatty acids, on leukocyte-endothelial cell adhesive interactions was evaluated:

Table 1:
A. AG (ultrarefined)
B. AG stearate (DS 1.7%)
C. AG palmitate (DS 1.7%)
D. AG decanoate (DS 2.6%)
E. galactan from fractional hydrolysis of AG (arabinose 1.5%)
F. AG dodecyl ether (DS 1.3%)

In Vitro Assay

The in vitro effects of Compound A–F listed in Table 1 on leucocyte and endothelial cell adhesion under physiological shear forces was examined as follows.

Human umbilical vein endothelial cells (HUVEC) were grown to confluence on the internal surface of collagen type I coated capillary tubes. Endothelial cells were stimulated for 4 hours with rIL-1β (10 ng, Genzyme), which upregulates adhesion molecules such as E-selectin within 4–6 hours. Neutrophils and lymphocytes were collected from normal human donors by venipuncture and separated from the blood on ficoll-histoplaque density gradients. The endothelial cell-coated tubes were then integrated into the closed-loop system. Leukocytes were infused into the assay system at a concentration of $1 \times 10^6 - 5 \times 10^6$ cell/ml in DMEM plus 20 mM HEPES. Shear forces of 1–3 dynes/cm$^2$ (standard representation of blood flow) were applied via a variable speed peristaltic pump, and interactions between the leukocytes and endothelial cells were monitored by video-microscopy. Comparisons were made of the binding of leukocytes and endothelial cells treated with the 6 compounds and untreated controls.

For lymphocytes, rolling interactions were established for ten minutes at which point the compounds were infused at increasing concentrations: 1 µg/ml, 10 µg/ml, and 100 µg/ml added at 5 minute time intervals. Interactions, from time 0 were observed and recorded to video tape for off-line analysis.

To observe the effects of the compounds on neutrophil adhesive interactions, the neutrophils were infused and allowed to establish rolling for two minutes before the addition of the compounds. The compounds were added in increasing 1 µg/ml, 10 µg/ml, and 100 µg/ml final concentrations at 2 minute intervals. The interactions were recorded to video tape.

Results

Lymphocytes

Binding curves illustrated that Compounds A–F had no significant effect on lymphocyte accumulation on the activated HUVEC monolayer. Averaged values of three experiments were used to generate a mean value binding curve and a smoothed fitted binding curve that showed no significant alteration of lymphocyte adhesion or rolling by these compounds.

Thus, compounds A–F did not significantly effect lymphocyte-HUVEC adhesive rolling interactions. Rolling interactions of lymphocytes involve multiple adhesion receptor ligand interactions including L- and E- selectin as well as α4/β1 and VCAM-1. Adhesive interactions by these pathways were not significantly altered in these assays.

Neutrophils

Binding curves for compounds A–F in the neutrophil-HUVEC adhesion study were obtained in addition to control binding curves. Each experiment was repeated three times. Compound A (repeated three times) caused an approximate 75% reduction in neutrophil adhesion during the time course but did not reduce binding to baseline even at concentrations of 10 µg/ml or 100 µg/ml. Compounds B and C, in both experimental repeats showed a consistent 90% or greater reduction in neutrophil adhesion beginning immediately upon addition of the compounds at their lowest concentration (1 µg/ml).

Thus, Compounds A, B, and C significantly blocked neutrophil rolling on activated HUVEC, while Compounds D, E, and F had no measurable effect. Rolling interactions of neutrophils involve multiple adhesion receptor ligand interactions including L- and E-selectin. These adhesive interactions were those most likely to have been disrupted by compounds A, B, and C. The concentration (1 µg/ml) at which B and C were effective in blocking neutrophil-HUVEC adhesion are equivalent to the minimal concentration at which mAb blockers of E-selectin are fully effective in preventing adhesion.

The arabinogalactan-containing compounds thus appear to selectively block neutrophil-endothelial cell adhesion at extremely low levels without blocking lymphocyte adhesion. Thus, the compounds are potentially useful in blocking acute inflammatory associated pathology generated by neutrophil recruitment to sites of potential ischemic reperfusion injury, or for the treatment of other disease processes that result in neutrophil recruitment such as burn associated pathology, heart attack, angioplasty, graft rejection and acute respiratory diseases.

Example 3: Synthesis of Water-soluble and Water-insoluble AG Palmitates

Dry, ultrarefined AG (10.28 g) was dissolved with heating in dry dimethyl sulfoxide (50 mL) at 100° C. Dry pyridine (25 mL) was added, followed by palmitic anhydride (3.0 g) and stirred until solution was complete. After 90 min. at 100°

C., the brown solution was cooled to room temperature, ice (5 g) was added with stirring and the resultant solution then added dropwise with stirring to redistilled isopropanol (500 mL). The resultant white powder precipitate was left overnight and then centrifuged, and the solid washed twice with isopropanol. The solid was dissolved in water (120 mL), concentrated to about 100 mL and then shaken with chloroform (100 mL). Three layers formed. The lower layer was separated and discarded and the upper two layers (the middle layer being a viscous emulsion) further washed twice with chloroform with intermdediate centrifugation. The upper layer was then dialyzed against running water for three days and freeze dried to yield 7.70 g of an off-white solid. The palmitate content was calculated from the PMR spectrum in $D_2O$ solution by relating the palmitate $CH_2$ signal at 1.26 ppm (s, 26 H) to the total glycose CH integration from 4.3 to 3.1 ppm, assuming that this represented 6 H per glycose unit. This integration indicated that 1.70% of the glycose units carried a palmitate ester group.

The semi-solid middle layer from the above solvent separation was further washed with water, centrifuged and freeze dried to a white, water-insoluble product (3.3 g), PMR analysis in d6 dimethyl sulfoxide at 70° C. with integration as above, indicated that 7.3% of the glycose units carried a palmitate ester group. This product was partly, but not completely soluble in boiling water.

Example 4: Synthesis of Water-soluble AG Palmitate

The preparation described in Example 3 was repeated, using less palmitic anhydride (1 g) and heating for 60 min. only. The product, after addition of ice, was added dropwise with stirring to isopropanol (500 mL). The resultant precipitate was filtered, washed with isopropanol, then boiled with several portions of chloroform, finally filtered and dried at 50°/1 mm. The product (8.12 g from 8.99 g of AG) was completely soluble in water at room temperature and PMR analysis indicated that 0.9% of the glycose units carried a palmitate ester group.

Example 5: Synthesis of Water-soluble AG Stearate

The procedure of Example 4 was repeated with stearic anhydride (2.0 g). Analysis of the final water-soluble product as above, indicated that 1.7% of the glycose units carried a stearate ester.

Example 6: Synthesis of the Dodecyl Ether of AG

Dry AG (2.0 g) was dissolved with heating in dry dimethyl sulfoxide (5 mL), cooled to room temperature and stirred for 15 min. with powdered sodium hydroxide (1 g). Dodecyl iodide (0.2 mL) was added, and the mixture stirred for 30 min. at room temperature. After filtration, the solution was poured into isopropanol (100 mL) with stirring, and the resultant white precipitate washed with isopropanol containing a little acetic acid. After further washing with isopropanol, the white solid was dissolved in water and dialyzed for several days before freeze drying. The product was analyzed by PMR in $D_2O$ solution as in Example 3 to show that 1.3% of the glycose units carried a dodecyl ether group.

Example 7: Formation of Oil-water Emulsions with Water-soluble Lipidated Arabinogalactan An aqueous solution of AG palmitate (2 mL, 1.0% solution, DS 1.7%) was mixed with safflower oil (4 g) and vigorously shaken. A uniform viscous emulsion formed and no separation of phases was evident after several days at room temperature.

When a 1% solution (2 mL) of the same AG palmitate was shaken with hexane (1 mL) the upper phase became extremely viscous and opaque and remained in this state for several days.

Example 8: Increased Solubility of Progesterone in Aqueous AG Decanoate

Progesterone was heated with water at 60° C. for 10 min, then held at 25° C. for 20 h. The filtered solution was analyzed by UV absorption at $\lambda$max 250 nm to show that the saturated solution contained $8.8 \times 10^{-4}$% dissolved progesterone.

When the above experiment was repeated with a 1% aqueous solution of AG decanoate (DS 2.59%) the saturated solution contained $4.7 \times 10^{-3}$% progesterone. In the UV analysis of the AG decanoate solution of the progesterone, the appropriate AG decanoate solution without progesterone was used as a spectrometer blank.

What is claimed is:

1. A method for treating diseases in animals and humans caused by infectious organisms comprising administering an effective amount of a water soluble compound, comprising arabinogalactan covalently attached to a lipophilic group, to alleviate the disease, wherein the method inhibits cell-adhesion of the organisms to cells in animals and humans.

2. The method of claim 1 wherein the disease is associated with neutrophil-endothelial cell adhesion.

3. The method of claim 1 wherein the arabinogalactan is isolated from a tree of the genus Larix.

4. The method of claim 1 wherein the lipophilic group is selected from the group consisting of fat soluble vitamins, phytosterols, terpenoids, phospholipids, glycerols, and natural or synthetic fats.

5. The method of claim 1 wherein the compound is administered in a composition comprising a pharmaceutically acceptable carrier.

6. The method of claim 1 wherein the compound comprises a fatty acid attached by an ester linkage to arabinogalactan.

7. The method of claim 1 wherein the compound interferes with the adhesion of neutrophils to endothelial cells.

8. The method of claim 1 wherein the method inhibits infection of cells.

9. The method of claim 8 wherein the compound is contacted with the cells.

10. The method of claim 1 wherein the infectious organisms are invading microorganisms.

11. The method of claim 1 wherein the method inhibits inflammatory response in cells.

12. The method of claim 11 wherein the compound is contacted with the cells.

13. The method of claim 11 wherein the inflammatory response is associated with a pathological state selected from the group consisting of rheumatoid arthritis, psoriasis, septic shock, atherosclerosis, thrombosis, ischemia, and reperfusion injury.

14. A method for treating diseases in animals and humans caused by infectious organisms comprising administering an effective amount of a composition comprising a lipid-arabinogalactan compound to alleviate the disease, wherein:

(a) the lipid portion of the compound has between about 4 and about 30 carbon atoms;

(b) the compound is water soluble;

(c) the compound has a degree of substitution no greater than about 15%; and (d) the lipid portion of the compound is a fatty acid attached by an ester linkage to arabinogalactan.

15. The method of claims 14 wherein the starting arabinogalactan is isolated from a tree of the genus Larix.

16. The method of claim 14 wherein the composition further comprises water and a compound that has low solubility in water, and wherein the lipid-arabinogalactan compound is present in an amount effective to enhance the water solubility of the compound that has low solubility in water.

17. The method of claim 14 wherein the composition further comprises water and a non-aqueous phase that has low solubility in water, wherein the lipid-arabinogalactan compound is present in an amount effective to form a stable emulsion.

18. The method of claim 14, wherein the composition further comprises an antigen.

* * * * *

UNITED STATES PATENT AND TRADEMARK OFFICE
CERTIFICATE OF CORRECTION

PATENT NO. : 6,258,796 B1  Page 1 of 1
DATED : July 10, 2001
INVENTOR(S) : Geoffrey N. Richards It is certified that error appears in the above-identified patent and that said Letters Patent is hereby corrected as shown below:

<u>Title page,</u>
Item [56], References Cited, OTHER PUBLICATIONS, please insert
-- Brennan et al., "The Envelope of Mycobacteria," *Annu. Rev. Biochem., 64*:29-63 (1995). --; and please insert -- Liu et al., "Fluidity of the Lipid Domain of Cell Wall from Microbacterium Chelonae," *Proc. Natl. Acad. Sci. USA, 92*:11254-11258 (1995). --.

Signed and Sealed this

Twelfth Day of November, 2002

*Attest:*

*Attesting Officer*

JAMES E. ROGAN
*Director of the United States Patent and Trademark Office*